US 7,456,960 B2

(12) United States Patent
Cerni et al.

(10) Patent No.: US 7,456,960 B2
(45) Date of Patent: Nov. 25, 2008

(54) PARTICLE COUNTER WITH IMPROVED IMAGE SENSOR ARRAY

(75) Inventors: Todd A. Cerni, Mead, CO (US); Dwight A. Sehler, Longmont, CO (US)

(73) Assignee: Particle Measuring Systems, Inc., Boulder, CO (US)

( * ) Notice: Subject to any disclaimer, the term of this patent is extended or adjusted under 35 U.S.C. 154(b) by 0 days.

(21) Appl. No.: 11/273,865

(22) Filed: Nov. 15, 2005

(65) Prior Publication Data

US 2006/0274309 A1   Dec. 7, 2006

Related U.S. Application Data

(60) Provisional application No. 60/687,777, filed on Jun. 6, 2005.

(51) Int. Cl.
*G01N 15/02* (2006.01)
(52) U.S. Cl. ...................................... 356/336; 356/338
(58) Field of Classification Search .................. 356/246, 356/335–343
See application file for complete search history.

(56) References Cited

U.S. PATENT DOCUMENTS

| | | | |
|---|---|---|---|
| 4,739,177 A * | 4/1988 | Borden ........................ | 250/574 |
| 4,798,465 A | 1/1989 | Knollenberg | |
| 5,282,151 A | 1/1994 | Knollenberg | |
| 5,565,984 A | 10/1996 | Girvin | |
| 2003/0020910 A1 * | 1/2003 | Peterson et al. ............. | 356/338 |
| 2005/0136548 A1 * | 6/2005 | McDevitt et al. ............ | 436/180 |

FOREIGN PATENT DOCUMENTS

WO   WO 2004/031742 A   4/2004

OTHER PUBLICATIONS

Knollenberg, R.G.; "The Design Of A High Sensitivity Large Sample Volume Particle Counter For Ultra Clean DI Water"; *Microcontamination 92 Conference Proceedings*; Santa Clara, CA; pp. 764-776; Canon Communications; 1992.

(Continued)

*Primary Examiner*—Tarifur R Chowdhury
*Assistant Examiner*—Tara S Pajoohi
(74) *Attorney, Agent, or Firm*—Greenlee Winner and Sullivan P.C.

(57) ABSTRACT

A particle counter for optically detecting an unconstrained particle of less than one micron in size suspended in a flowing liquid includes a sample chamber having a fluid inlet and a fluid outlet; a laser module producing a laser beam; a beam shaping optical system providing a multiple laser beam pattern in the sample chamber, and a CMOS optical detector located to detect light scattered by the particles in the sample chamber. The particle counter has a particle sensing area within the sample chamber in which the intensity of light is at least 10 Watts/mm$^2$, the sensing area having an area of 0.5 square mm or more. The detector has thirty or more detector array elements. In the preferred embodiment, the laser optical system reflects and refocuses the laser beam to effect multiple passes of the same laser beam through the sensing area.

48 Claims, 6 Drawing Sheets

OTHER PUBLICATIONS

Knowlton, D.K.; "Iniviscid Jet Technology For Monitoring Particles In Fluids"; *Proceedings 1998 Institute of Environmental Sciences And Technology*; pp. 34-39; 1998.

Cerni, T.A.; "High Sensitivity, High Sample Rate, Aerosol Optical Particle Counter"; *Clean Technology*; vol. 11, No. 6; pp. 12-14; 2001.

http://www.micron.com/products/imaging/products/MT9M413.html; Micron Document No. MT9M43C365TC.fm—ver. 3.0; Jan. 2004 EN.

* cited by examiner

PARTICLE COUNTER WITH IMPROVED IMAGE SENSOR ARRAY

RELATED APPLICATIONS

This application claims priority to U.S. Provisional Application No. 60/687,777 filed Jun. 6, 2005.

FIELD OF THE INVENTION

The invention in general relates to systems that utilize light scattering principles to detect and count undesirable single particles of less than one micron In size in fluids, which systems are generally referred to in the art as optical particle counters (OPC). More particularly, the invention relates to such a particle counter that utilizes a two-dimensional multi-element detector array.

BACKGROUND OF THE INVENTION

Optical particle counters (OPCs) are used to detect and measure the size of individual particles suspended in a fluid. Generally, particle counters are designed to detect particles of less than one micron in size. Each particle that is detected is counted, and an indication of the number of particle counts within a channel, with each channel corresponding to a particular size range, is provided. For particle counters to operate effectively, the density of particles in the fluid must be small enough that the particles are considered to be contaminants in the fluid. That is, it is important to distinguish the science of particle counting from other scientific fields, such as photometry and cytometry, which also utilize scattered light, but in which the density of the particles in the fluid is so large that they are essentially the fluid itself. These latter systems rely on collecting scattered light from millions, billions, and more particles; therefore, their principles of operation are very different from the principles used in particle counters.

Particle counters are commonly used to detect contaminant particles in the fluids used in manufacturing clean rooms in the high-tech electronics and the pharmaceutical industries. Generally, it is not possible to detect all the particles in the fluid of interest, since the amount of fluid is quite large. Thus, small samples of the fluids used in the manufacturing processes are diverted to the particle counters, which sound an alarm if the number and/or size of the particles detected is above a predetermined threshold. Since a small sample of the manufacturing fluid is generally not completely representative of the entire volume of the manufacturing fluid, statistics are used to extrapolate the state of the manufacturing fluid from the sample. The larger the sample, the more representative it is, and the more quickly an accurate determination of the number and size of particles in the manufacturing fluid can be made. It is desirable for a particle counter to detect particles as small as possible, as fast as possible, in as large a sample as possible.

Figure 1:
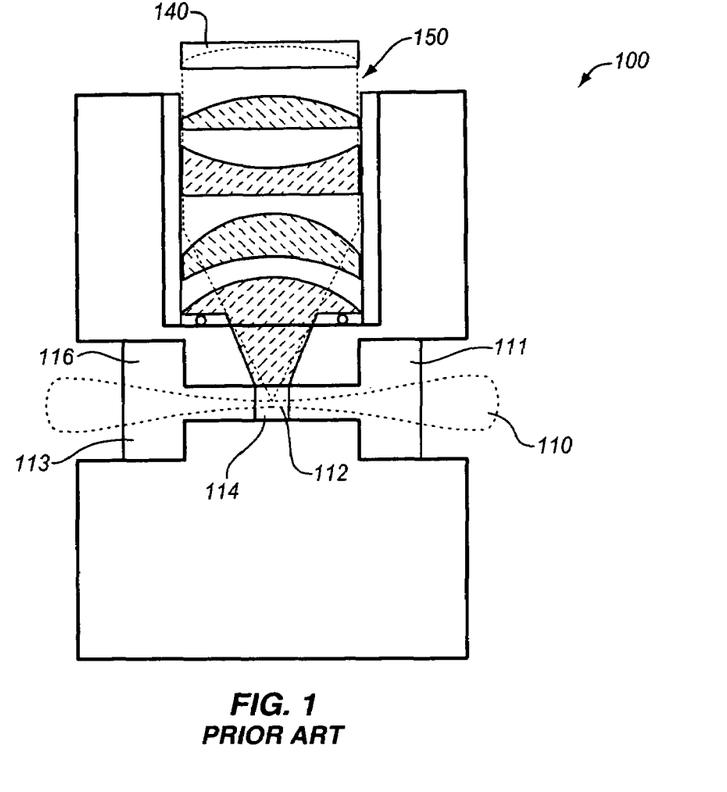
FIG. 1 shows a conventional liquid optical particle counter according to the invention.

FIG. 1 shows a schematic depiction of the optical design of a conventional liquid OPC 100. The laser beam 110 passes through windows 111 and 113 of a sample cell 116 and is focused to a narrow waist 112 in the liquid flow 114 of the sample cell 116. In this cell, the liquid flows in a direction out of the paper. The very high laser irradiance (power per area) at the laser beam waist 112 is a key element in being able to detect particles less than 100 nm in diameter. The laser radiation scattered by each particle is focused onto a detector 140 through a large numerical aperture, complex imaging system 150. The use of high power illumination generally enhances particle detection. Specifically, higher power levels generally enable the detection of smaller particles than lower power systems. Higher power levels also generally permit particles of a given size to be detected more quickly. Thus, high power lasers are generally used as the light source in particle counters.

Another constraint that must be taken into account in particle counting is the background noise due to scattering of light by the molecules of the fluid in which the contaminant particles are contained. While the amount of light scattered by each molecule of fluid is small, the number of fluid particles is extremely large. For example, there are approximately $10^{16}$ air molecules per cubic mm at atmospheric pressure. The light scattered by the fluid molecules cannot be eliminated. This light creates a background of molecular scattering noise that masks the signal from the contaminant particles.

In U.S. Pat. No. 4,798,465 issued Jan. 17, 1989 to Robert G. Knollenberg, which patent is hereby incorporated by reference, it was demonstrated that the background molecular scattering noise can be reduced by use of a one-dimensional detector array. When the sample volume is imaged onto such a detector array, the molecular scatter noise is divided by the number of elements. However, if the detector optics are correctly designed, the scattered light signal from the particle is imaged onto one detector element. Since this invention, the state-of-the-art OPC typically has employed a twenty-element array. The net result is that the use of a twenty-element detector array, in place of a single-element detector, yields the same signal-to-noise benefit as increasing the laser irradiance by twenty-fold.

U.S. Pat. No. 5,282,151 issued Jan. 25, 1994 to Dr. Robert Knollenberg, which patent is hereby incorporated by reference, proposed the use of a high-density two-dimensional CCD (Charge Coupled Device) detector. Knollenberg proposed that in this design, like the one-dimensional array design, the signal-to-noise advantage theoretically should be proportional to the number of detector elements. Since CCD arrays typically contain greater than 1,000,000 elements, CCD arrays would appear to offer a promising design option for boosting OPC performance. However, the design was not successful and never became a commercial product. Fundamentally, the geometry of the conventional optical particle counter as shown in FIG. 1 did not allow for the effective use of two-dimensional detector arrays. Thus, for the last decade and a half, improvements in liquid OPC performance, at particle sizes less than 100 nm, have been achieved through the use of higher powered, more expensive lasers.

The users of particle counters, such as high-tech electronics manufacturers, are continually making advances that permit smaller and smaller device parameters. Modern semiconductor chips are complex three-dimensional structures of transistors and other electrical components. Particles in de-ionized water (DIW) and other process fluids can create defects by clinging to wafers, thus interfering with photolithography, as well as physical and chemical vapor deposition processes. The purity of DIW is particularly important, because DIW is used as the final rinse in most fabrication processes before proceeding to the next process. The prevailing opinion in the semiconductor industry is that the maximum allowable diameter of particulate contaminants in DIW equals one-half the semiconductor line width. The International Technology Roadmap for Semiconductors (ITRS) specifications, consistent with this guideline, for allowable particulate contamination in DIW are given in Table A, where hp90 and hp65 refer to 90 nm and 65 nm linewidths, respectively. Over the last two years, conventional optical particle counter (OPC) designs have been hard pressed to keep pace with the ITRS DIW sensitivity specifications, and conventional designs have no hope of achieving future targets.

TABLE 1

ITRS Particle Contamination Specifications for DI Water

| | Production Year | | | | | | |
|---|---|---|---|---|---|---|---|
| | 2003 | 2004 | 2005 | 2006 | 2007 | 2008 | 2009 |
| Technology Node | | hp90 | | | hp65 | | |
| Critical Particle Size | 50 nm | 45 nm | 40 nm | 35 nm | 33 nm | 29 nm | 25 nm |
| Particle Concentration | <0.2/ml | <0.2/ml | <0.2/ml | <0.2/ml | <0.2/ml | <0.2/ml | <0.2/ml |

Therefore, there exists no known, practical, liquid OPC design which can provide a significant increase in sensitivity over the conventional design depicted in FIG. 1 using the array described by Knollenberg in U.S. Pat. No. 4,798,465. Furthermore, this conventional liquid OPC design is unable to keep pace with the International Technology Roadmap for Semiconductor given in Table 1.

Accordingly, there is a need in the art for a particle counter system and method that can more effectively process out molecular background noise and permit smaller contaminant particles to be detected. In particular, there is a need in the art for a particle counter system that is able to effectively utilize a sensing array larger than twenty array elements.

BRIEF SUMMARY OF THE INVENTION

The present invention advances the art and helps to overcome the aforementioned problems by providing an optical particle counter that includes a CMOS imager array.

The present invention advances the art and helps to overcome the aforementioned problems by providing an optical particle counter in which a plurality of laser beams define a sensing region in a fluid flow. In this disclosure, the term "beams" and similar terms refer to either an architecture in which a single laser generates a laser beam which passes through the flow and then is redirected back through the flow one or more times, an architecture in which the plurality of beams are generated by a plurality of lasers, or a combination of the two architectures. Preferably, the beam is redirected with one or more mirrors, though an optical fiber or other redirection device may be used.

The present invention advances the art and helps to overcome the aforementioned problems by providing an optical particle counter having a particle sensing area in which the intensity of light is at least 10 W/mm$^2$ (watts per square millimeter) in a sensing area having an area of 0.5 square millimeters (mm) or more.

The invention provides an optical particle counter for optically detecting unconstrained particles of less than one micron in size suspended in a flowing fluid, the optical particle counter comprising: a sample chamber having a fluid inlet and a fluid outlet; a source of light; a light-directing optical system directing the light through the sample chamber, an optical collection system located to collect light scattered by the particles in the fluid flowing through the sample chamber, and a detection system located to detect light collected by the optical collection system, the detection system including an optical detector producing an electric signal characteristic of the number of the particles of less than one micron in size which are detected; wherein the optical detector comprises a CMOS imager. Preferably, the fluid is a liquid and the source of light comprises a laser. Preferably, the fluid flows through the sample chamber in a first direction and the detector detects light scattered from the particles in the first direction. Preferably, the flow cell includes flow cell walls, the optical collection system has an optical axis, and, in a direction along the optical axis opposite to the direction of the detector from the sample chamber, the flow cell has no flow cell wall from which stray light sufficient to create optical noise can enter the detector. Preferably, the light-directing optical system comprises redirection optics for directing and refocusing the laser beam through the sample chamber a plurality of times. Preferably, the redirection optics comprises a plurality of mirrors. Preferably, the plurality of mirrors are located to direct the laser beam through the sample chamber ten or more times. More preferably, the plurality of mirrors are located to direct the laser beam through the sample chamber twenty-five or more times. Preferably, the light collecting system has an optical axis, and the plurality of laser beams pass through the sample chamber lie in a plane perpendicular to the optical axis. In one embodiment, the source of light comprises a plurality of lasers producing a plurality of the laser beams, and the light-directing optical system comprises an optical system for directing the plurality of laser beams through the sample chamber.

The invention also provides a method of detecting unconstrained particles of less than one micron in size in a flowing fluid, the method comprising: flowing the fluid containing the unconstrained particles of less than one micron in size; directing a laser beam through the fluid flow, collecting light scattered by the particles in the fluid; and detecting the collected light with a CMOS imager and outputting a signal from the CMOS imager that is characteristic of a parameter of the particles. Preferably, the directing comprises passing the laser beam through the fluid flow and refocusing the beam a plurality of times. Preferably, the passing comprises passing the laser beam through the fluid flow three or more times in the same plane. Preferably, the collecting comprises collecting the scattered light about an optical axis perpendicular to the plane. Preferably, the collecting comprises collecting the light about an optical axis, and the flowing comprises flowing the fluid in the direction of the optical axis.

In another aspect, the invention provides a device for optically detecting unconstrained particles of less than one micron in size suspended in a flowing fluid, the device comprising: a sample chamber having a fluid inlet and a fluid outlet; a multiple beam laser optical system for providing a plurality of laser beams in the sample chamber, an optical collection system located to collect light scattered by the particles of less than one micron in size in fluid flowing through the sample chamber, and a detection system located to detect light collected by the optical collection system, the detection system including an optical detector producing an electric signal characteristic of the number of the particles detected; wherein the optical detector has thirty or more optical detector elements. Preferably, the multiple beam laser optical system comprises a laser producing the laser beam and an optical redirection device for directing and refocusing the laser beam back through the sample chamber after it has passed through the chamber once. Preferably, the optical redirection device comprises a mirror, and more preferably, a plurality of mirrors. Preferably, the optical collection system has an optical axis and the laser beams lie in a plane perpendicular to the optical axis. Preferably, the sample chamber, the collection optics, and the detector define a sensing region, the sensing region having a cross-sectional area in a plane parallel to the laser beams, which area is 0.5 square millimeters or more. More preferably, the area is 1 square millimeter or more. Most preferably, the area is 2 square millimeters or more. Preferably, the multiple beam laser optical system comprises a plurality of lasers providing the laser beams. Preferably, the optical detector comprises a CCD pixel array, and more preferably, a CMOS pixel array. Preferably, the optical detector comprises a two-dimensional pixel array.

In a further aspect, the invention provides a method for optically detecting unconstrained particles of less than one micron in size suspended in a flowing fluid, the method comprising: flowing the fluid containing the unconstrained particles of less than one micron in size; directing a plurality of laser beams through the fluid flow, collecting light scattered by the particles in the fluid; and detecting the collected light and outputting a signal characteristic of a parameter of the particles. Preferably, the directing comprises producing a laser beam, passing the laser beam through the fluid flow, and redirecting and refocusing the laser beam back through the fluid flow.

In still a further aspect, the invention provides a device for optically detecting unconstrained particles suspended in a flowing fluid, the device comprising: a sample chamber having a fluid inlet and a fluid outlet; a light source for providing one or more light beams in the sample chamber; an optical collection system located to collect light scattered by the particles in the light beams in the sample chamber; and a detection system located to detect light collected by the optical collection system; the detection system including an optical detector producing an electric signal characteristic of the number of the particles detected; the optical detector has thirty or more optical detector elements; and the one or more light beams, the optical collection system, and the optical detector defining a particle sensing area within the sample chamber in which the intensity of light is at least 10 watts per square millimeter, the sensing area having an area of 0.5 square mm or more. Preferably, the sensing area is one square mm or more, and more preferably, two square mm or more. Preferably, the light source comprises a laser. Preferably, the light source includes a plurality of mirrors. In one embodiment, the light source comprises of plurality of lasers. Preferably, the optical detector comprises a CCD pixel array, and more preferably, a CMOS pixel array. Preferably, the optical detector comprises a two-dimensional pixel array. Preferably, the fluid flows through the sample chamber in a first direction and the detector detects light scattered from the particles in the first direction. Preferably, the flow cell includes flow cell walls, the optical collection system has an optical axis, and, in a direction along the optical axis opposite to the direction of the detector from the sample chamber, the flow cell has no flow cell wall from which stray light sufficient to create optical noise can enter the detector.

The invention dramatically increases the signal-to-noise ratio possible in optical particle counters. Thus, particles can be counted faster and/or smaller particles can be detected. The above and other advantages of the present invention may be better understood from a reading of the following description of the preferred exemplary embodiments of the invention taken in conjunction with the drawings in which:

DETAILED DESCRIPTION OF THE INVENTION

In this disclosure, the term "light" is not limited to visible radiation but is used in a broad sense meaning any electromagnetic radiation, including infrared, ultraviolet, extreme ultraviolet, and x-ray radiation. The term "stray light" includes any light that is not wanted, i.e., light that is not light scattered from particles but which can get into the collection optics. Multiple reflected light is a significant source of stray light in prior art particle counters. That is, light that is reflected once, scattered from a scattering source, or diffracted by a lens or aperture can usually be blocked out by other apertures or absorbing black walls even in conventional particle counters because the source of the unwanted light is known. However, multiple reflections make it difficult to determine the direction of the light, and thus often cannot be apertured or otherwise blocked out. As will be discussed below, the invention provides a unique system and method so that stray light is significantly reduced. Further, it should be noted that particle counters as disclosed herein are designed to be able to detect single particles which are unconstrained in a flowing fluid as distinguished from other systems that detect and analyze the particles of the fluid itself, clouds of particles suspended in a fluid, or particles which are constrained in the fluid, such as constrained to flow in a single line past a light beam. Those skilled in the art recognize that it is a much more difficult task to detect and size single particles flowing unconstrained in a fluid, particularly particles of less than one micron in size; therefore, the art of particle counting involves different technology than these other particle detection and analysis systems.

The highest sensitivity OPCs are designed to be molecular scatter noise limited, through suppression of all other noise sources. OPCs of this class operate at the theoretical performance limit, and their signal-to-noise ratio (SNR) is given by Equation (1), adapted from Knowlton, D. K., 1998: "Inviscid Jet Technology For Monitoring Particles In Fluids", *Proceedings* 1998 *Institute Of Environmental Sciences And Technology*, pp 34-39, and Cerni, T. A, 2001: "High Sensitivity, High Sample Rate, Aerosol Optical Particle Counter", *Clean Technology*, Vol. 11, No. 6, pp. 12-14, which are hereby incorporated by reference to the same extent as though fully disclosed herein:

$$SNR = \sigma_P \{ [cPN_E]/[WHS_R] \}^{0.5} \quad (1)$$

where $$c = (\eta_O \eta_D)/(\sigma_M \rho_M), \quad (2)$$

and $\sigma_P$=Particle scatter cross section (cm$^2$),
P=Laser power (W),
$N_E$=Number of detector elements,
W=Laser beam width (cm),
H=Laser bean height (cm),
$S_R$=Sample rate (L/min),
$\eta_O$=Optical system efficiency ($S_R$),
$\eta_D$=Detector responsitivity (photon/J),
$\sigma_M$=Molecular scatter cross section (cm$^2$), and
$\rho_M$=Molecular density (cm$^{-3}$).

It can be seen from Equation (1) that a twenty-fold increase in the number of detector elements that are molecular scatter noise limited has the same effect as a twenty-fold increase in laser power. One is tempted to conclude that a very large, one-dimensional or two-dimensional detector array would yield vastly improved performance over the twenty-element APD detector array, which currently is state-of-the-art. However, as shown in FIG. 1, the laser beam 110 rapidly diverges on both sides of the very small laser beam waist 112, which typically limits the useful length of the laser beam to a few millimeters (mm). This beam divergence yields two undesirable effects: it reduces the laser irradiance and increases the size of the particle image. The former decreases the ability to detect small particles. The latter causes the image to be spread over several detector elements, or requires larger detector elements, both of which decrease the SNR, and decreases the ability to detect small particles. This disclosure describes the first effective use of large, two-dimensional detector arrays in an OPC design by providing a variety of possible OPC designs that are able to take advantage of Equation (1).

Figure 2:
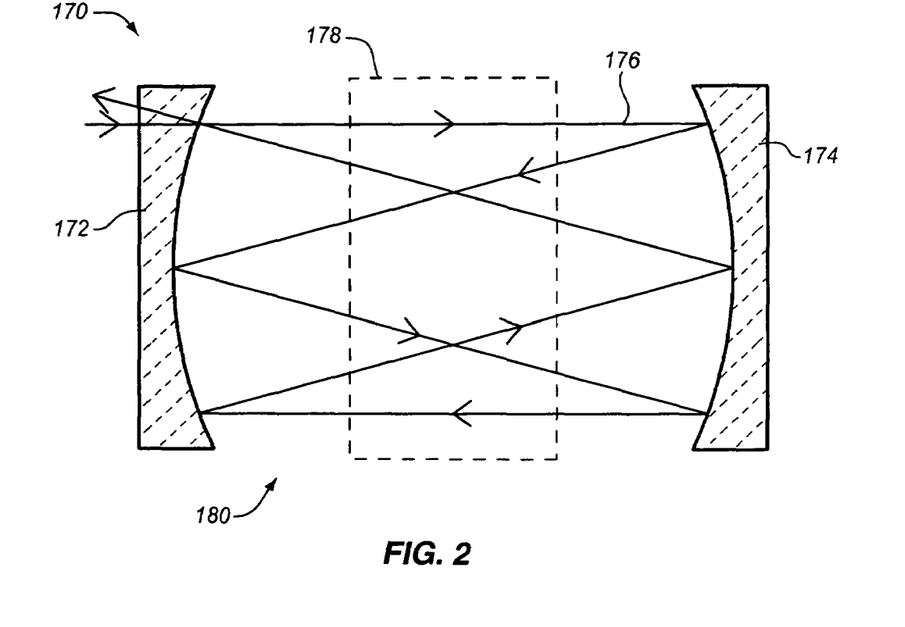
FIG. 2 illustrates the reflection and refocusing of a laser beam by a pair of mirrors according to the invention to produce a multiple laser beam pattern.

A preferred aspect of the OPC design according to the invention is shown in FIG. 2. This design takes advantage of the fact that, for example, for a DIW OPC, the laser beam power exiting the sample cell can be as high as 99% of the power entering the cell. For the conventional design depicted in FIG. 1, the laser beam is absorbed on a beam dump after exiting the sample cell. The preferred OPC design 170 according to the invention shown in FIG. 2 utilizes a pair of concave mirrors 172, 174 to repeatedly reflect and refocus the laser beam 176, such that the laser beam passes many times through the sample cell 178, with each pass duplicating the first, very small waist. Preferably, all the beam passes lie in a single plane. It is important that each time the laser beam 176 is redirected, it is also refocused; otherwise, the beam would diverge to such a size that the intensity would be reduced so much that the system's ability to count and size particles would be significantly negatively impacted.

Figure 3:
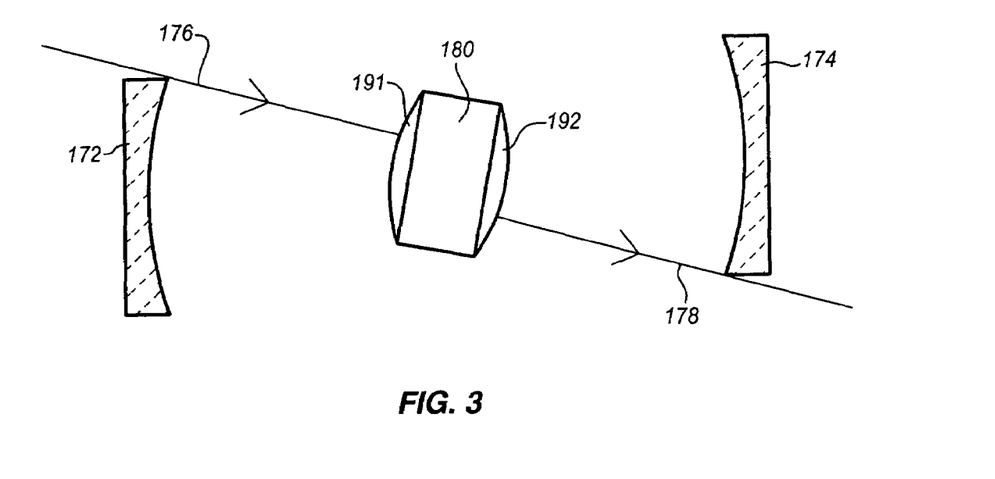
FIG. 3 illustrates the arrangement of the mirrors and flow cell for a multiple beam flow cell according to the invention.

When one places a water sample cell 178 between the two concave mirrors 172, 174, the multiple beam pattern 180, with repeated very small laser waist, is badly distorted due to refraction at the air/glass and glass/water interfaces. This distortion can be entirely eliminated if one replaces the sample cell windows with fused silica (glass) lenses 191, 192, as illustrated in FIG. 3. Preferably, the water flows through the sample cell 180 perpendicular to the page and perpendicular to the plane of the laser beams. The entry beam is shown at 176 and the exiting beam at 178. The multiple beam pattern is then viewed by a large, two-dimensional detector array through appropriate detector focusing optics similar to those depicted in FIG. 1. Since the refractive index of fused silica is close to that of water, losses due to reflection at the water/fused silica boundaries are very small. If one uses a visible laser, the water absorption losses are also very small. For a laser operating at 660 nm, and a sample cell water path length of 0.7 cm, these two losses yield a transmission of 0.994 for a single pass through the cell, or 0.829 for 27 passes through the cell. Furthermore, the additional optical losses at the two mirrors and the two air/fused silica interfaces can also be made very small through the application of thin film high reflectivity and anti-reflection optical coatings, respectively.

Figure 4:
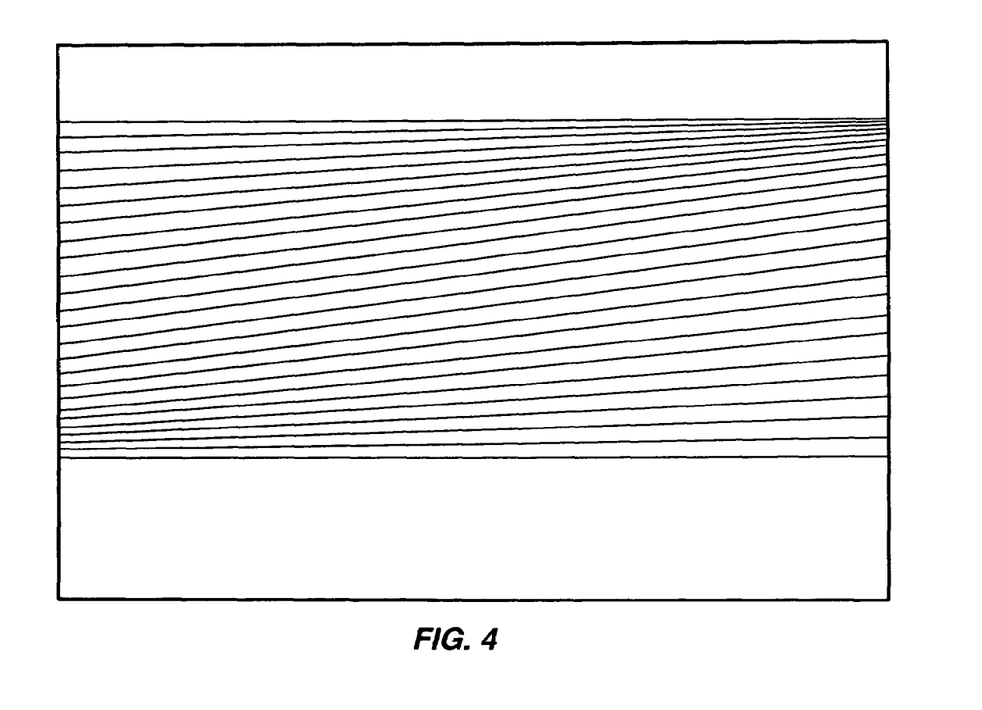
FIG. 4 is a depiction of a photograph of a multiple beam array according to the invention.

FIG. 4 is an illustration of an actual high resolution photograph of the laser beam pattern in the water produced by the optical design depicted in FIG. 3, implemented with a red visible (660 nm) laser diode and with a lens separation of 1.3 centimeters (cm) and a mirror separation of 10 cm. Because the photograph has been converted into a drawing, it is similar to a negative of the actual photograph. That is, the dark parts in the drawing are the lightest parts of the photograph, and the light parts in the drawing are dark in the photograph. The foregoing structure resulted in a 56 μm diameter laser beam waist in the center of the water sample cell 180 for each of 27 laser beams shown. The photograph illustrated in FIG. 4 was recorded with a 6 Megapixel Nikon D70 digital camera, equipped with a Nikkon 60 mm micro lens and a 2× teleconverter. The camera resolution was 7 μm. The portion of the beam pattern shown in FIG. 4 measures 2.7×7.0 mm. Laser beam divergence over these dimensions is small, because the two concave mirrors refocus the beam after each reflection and reproduce the laser waist of the first beam. The laser beam pattern shown in FIG. 4 requires precise alignment of the two concave mirrors and the water sample cell. This was accomplished with rigid micro-positioners, which allow for 5 degrees of freedom. Lens and mirror separations smaller than those given in FIG. 3 can be used to yield a laser waist less than 24 μm diameter with more than 30 laser beams. In the preferred embodiment, the area over which the beams are spread in FIG. 4 is 1.5 mm to 3 mm in the vertical direction and 4 mm to 5 mm in the horizontal direction. Optical systems of the type described in this disclosure can increase the effective number of molecular scatter limited detector elements to greater than 10,000, thus yielding a large increase in OPC sensitivity.

Figure 5:
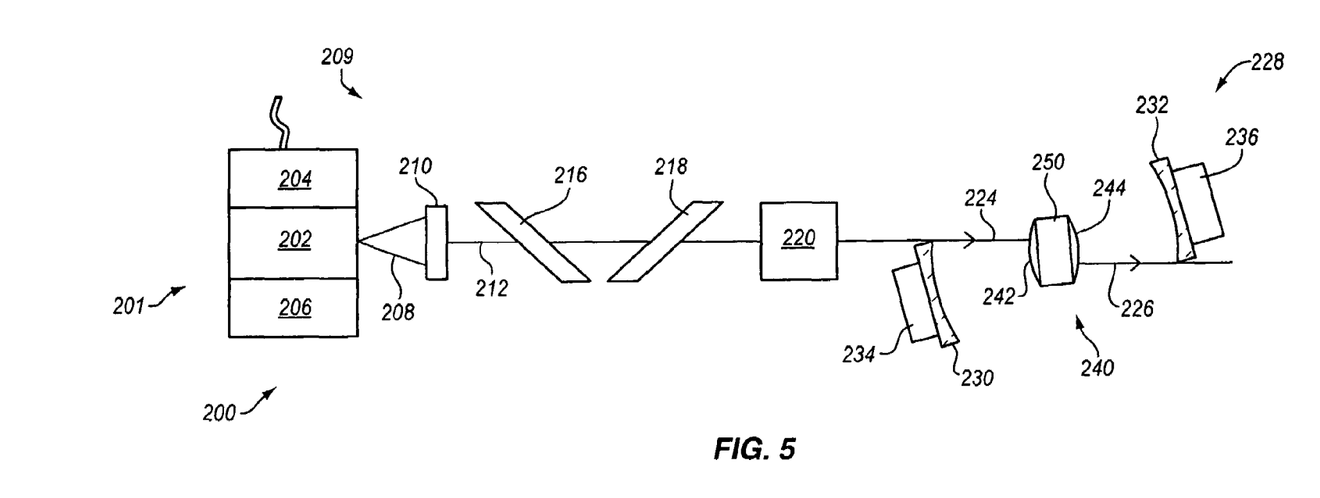
FIG. 5 is a block diagram of the preferred embodiment of an optical particle counter according to the invention.

Turning now to FIG. 5, a block diagrammatic illustration of an optical particle counter 200 according to the invention is shown. OPC 200 includes a laser module 201, beam configuration optics 209, and flow cell optics 228. Laser module 201 includes laser 202, laser electronics 204, and heat sink 206. Beam configuration optics 209 includes collimating lens system 210, anamorphic prisms 216 and 218, and focusing lens system 220. Flow cell optics 228 includes mirrors 230 and 232, mirror positioners 234 and 236, and flow cell 240 including window/lenses 242 and 244 enclosing flow cell volume 250. Laser 202 produces an uncollimnated beam 208, which is collimnated by lens system 210 to produce laser beam 212. Anamorphic prisms 216 and 218 change the beam cross-section from an elliptical cross-section to a circular cross-section. Focusing system 220 produces the entry beam 224 which is reflected and refocused by mirrors 230 and 232 as described above and exits at 226.

Figure 6:
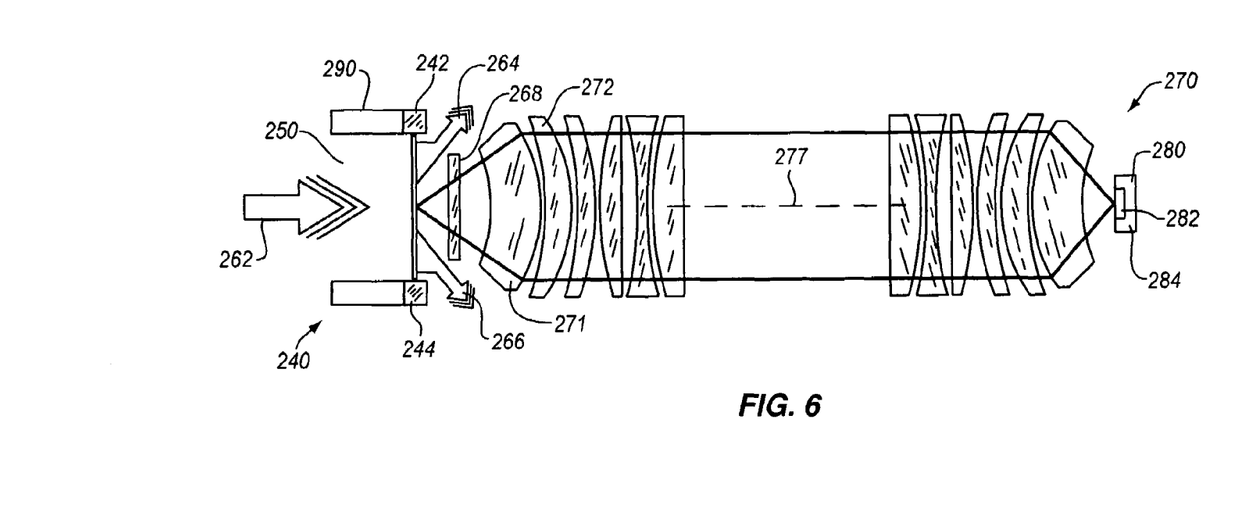
FIG. 6 is an illustration showing the relationship of flow cell, collection optics, and image sensor in the embodiment of FIG. 5.

In the preferred embodiment of the OPC 200, the fluid in which the particles are to be counted flows through flow cell volume 250 in a direction out of the paper in FIG. 5. The light scattered by the particles is also collected in a direction out of the paper, therefore, it is not shown in FIG. 5, but is shown in FIG. 6. This design of the collection optics is similar to that shown in Knollenberg, R. G., 1992: "The Design Of A High Sensitivity Large Sample Volume Particle Counter For Ultra Clean DI Water", *Microcontamination 92 Conference Proceedings*, Santa Clara, Calif., pp. 764-776, Canon Communications, which is hereby incorporated by reference to the same extent as though fully disclosed herein. The flow cell 240 according to the invention is shown generally in FIG. 6 and is shown in detail in FIGS. 7-10. Referring to FIG. 6, the fluid enters in the direction 262, which is the direction out of the paper in FIG. 5, and exits at the sides of the flow cell 240 at 264 and 266. A window 268 seals the flow cell volume from the collection optics 270, which preferably comprises a plurality of lenses 271, 272, etc., as known in the art. The collection optics 270 focuses the scattered light on detector 280, which includes two-dimensional detector element array 282 and detector electronics 284.

Figure 7:
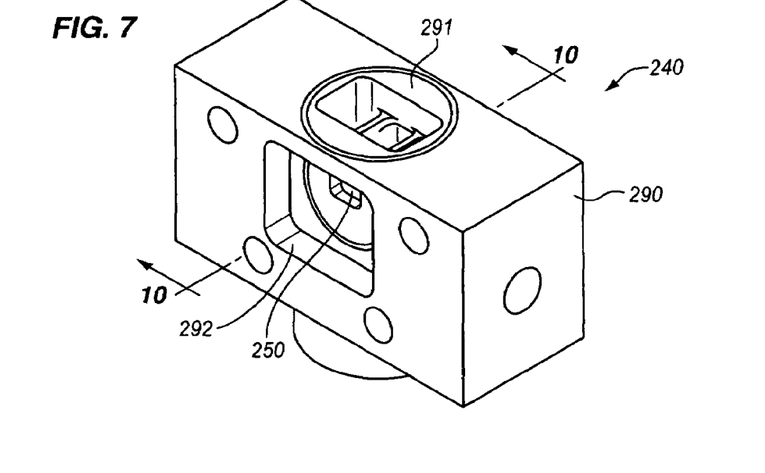
FIG. 7 is a perspective view of the flow cell of FIG. 5.
Figure 8:
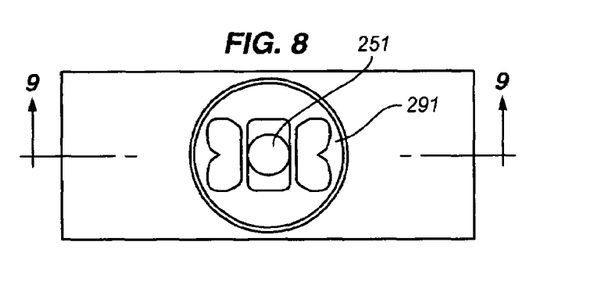
FIG. 8 is a top plan view of the flow cell of FIG. 5.
Figure 9:
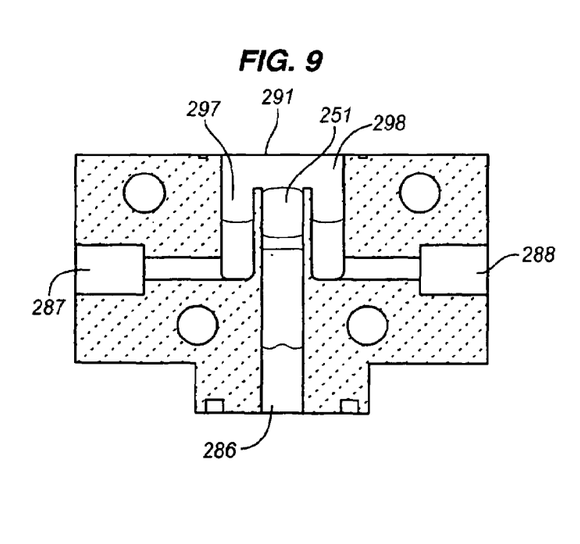
FIG. 9 is a cross-sectional view of the flow cell of FIG. 5 taken through the line 9-9 of FIG. 8.
Figure 10:
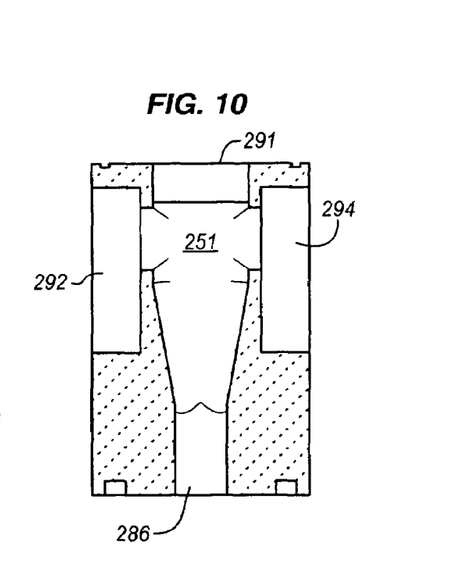
FIG. 10 is a cross-sectional view of the flow cell of FIG. 5 taken through the line 10-10 of FIG. 5.

The detailed structure of housing 290 flow cell 240 is shown in FIGS. 7-10. FIG. 7 is a perspective view of the flow cell housing 290, FIG. 8 is a top plan view, FIG. 9 is a cross-sectional view taken through the line 9-9 of FIG. 8, and FIG. 10 is a cross-sectional view taken through the line 10-10 of FIG. 5. Housing 290 has an optics port 291, window openings 292 and 294, fluid entrance port 286, and fluid exit ports 287 and 288. As best seen in FIGS. 9 and 10, the fluid flows upward through flow view volume 251, then downward through flow channels 297 and 298 to exit ports 287 and 288, respectively.

Figure 11:
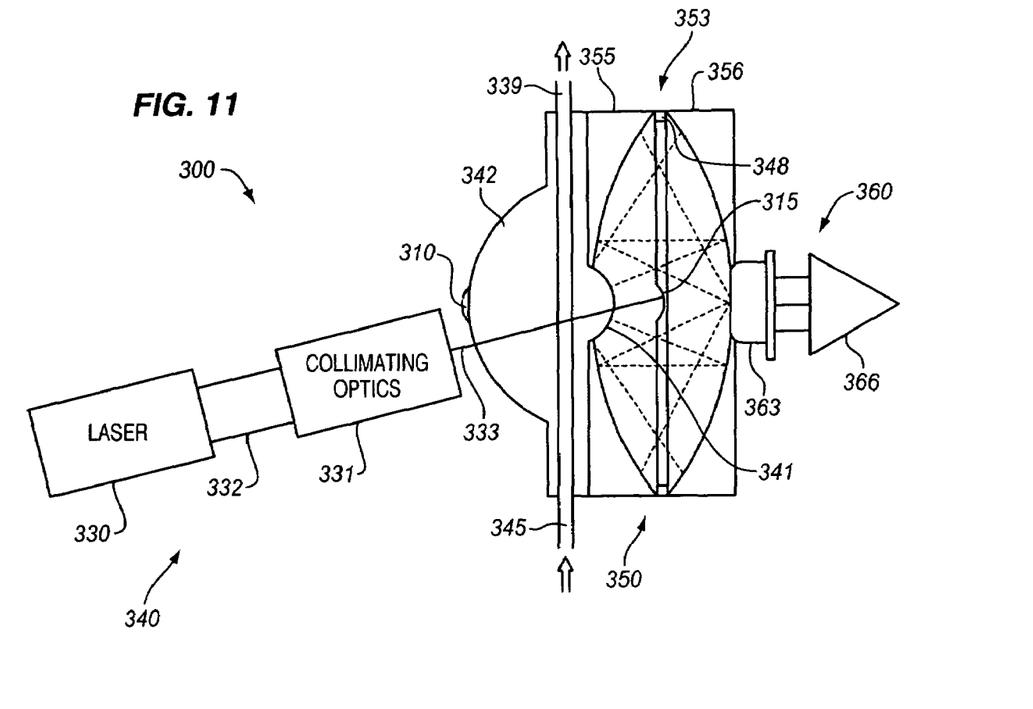
FIG. 11 shows another embodiment of a liquid particle counter according to the invention.

FIG. 11 shows another exemplary liquid particle counter 300 according to the invention. The embodiment of FIG. 11 is a modification of a liquid particle counter as described in U.S. Pat. No. 4,728,190 issued Mar. 1, 1998 to Robert Knollenberg and entitled "Device And Method For Optically Detecting Particles In A Fluid", which patent is incorporated by reference as though fully disclosed herein. The modifications include a modified illumination system 340, a modified collection system 350, and a modified detector 360. In the embodiment in FIG. 11, the illumination system 340 is shown in the same plane as the collection system 350 and detector system 360. However, in the most preferred form of this embodiment, the illumination system 340 is rotated ninety degrees about an axis through the flow passage 345 so that the collection system 350 and detection system 360 are at right angles to the illumination system 340. Illumination system 340 includes laser 330 producing uncollimnated laser beam 332, collimating optics 331 producing collimated laser beam 333, liquid capillary 339 having fluid passage 345, entry lens (window) 342, exit lens 341, mirrors 310 and 315, and mirror support band 348. Imaging system 350 (collection optics) includes parabolic mirrors 355 and 356. Detection system 360 includes detector array 363 and signal processing electronics 366. The embodiment in which the illumination system 340 is at right angles to the collection system 350 and detection system 360 is preferred because then the plane of the beam pattern is perpendicular to the collection optics, making it easier to spread the image of the area of the beam pattern, which is the area where particles will be detected, onto a large, two-dimensional array. The embodiment of FIG. 11 lends itself to a large, one-dimensional array, or a two-dimensional detector array where the dimension in the plane of the figure is longer than the dimension perpendicular to the plane of the figure. Another possible embodiment is one in which the illumination and collection optics are similar to those in U.S. Pat. No. 4,728,190, referenced above, but the detection optics is a two-dimensional detector element array as described below.

It should be understood that particle counters 100, 300 are exemplary to provide examples of particle counters with which the detector array and signal processing circuitry of the invention may be used. However, the invention may be incorporated into many other particle counters, and many variations on the designs disclosed may be used. As just a few examples, mirrors may be substituted for lenses and visa-versa, and the collecting optics may collect from any direction, since light is scatted from the particles in all directions. The detector array and signal processing circuitry may be used with any other particle counter system known in the art.

Either CCD (Charge Coupled Device) or CMOS (Complementary Metal Oxide Semiconductor) detector arrays are preferred for the detector array 282, 363, 423. Both types of arrays have been known for more than a decade. In U.S. Pat. No. 5,282,151, Robert Knollenberg disclosed the use of a high-density CCD (Charge Coupled Device) detector array for OPC applications. CCD and CMOS arrays both integrate the radiation signal for a period of time before unloading the data and initiating signal integration for the next frame. Further, each of the two systems has their own particular advantages. For example, CCD arrays provide better image quality, quantum efficiency, fill factor and pixel size, have lower noise and dark current, and, in the view of some, are overall more economical. CMOS arrays can implement 100% of the analogue signal processing on the detector chip, which can reduce total system cost and instrument development time. CMOS is also a lower cost semiconductor fabrication process, because CMOS architecture is used in 90% of all chips. We have found, however, that for optical particle counters, CMOS has several advantages not known up to now. For example, OPC design should use an integration time which is matched to the time it takes a particle to transit the laser beam. For the OPC designs discussed in this disclosure, this translates to an integration time on the order of one msec. CCD arrays utilize a parallel-to-serial charge shift register for data download, which we have found to be too slow for an OPC. CMOS arrays, however, accomplish charge to voltage conversion at each pixel, such that the data can be downloaded in any order, yielding a significant speed advantage in OPC applications, particularly for partial frames. Furthermore, CMOS arrays do not suffer from smear or blooming of images, which is common to CCD arrays. This is not a problem for many applications, but we have found it to lead to a lower SNR in OPCs. Therefore, CMOS arrays are preferred to CCD arrays for OPC applications, and particularly for implementation of the novel multiple laser beam optical design described in this disclosure, though CCD arrays may be used.

Figure 12:
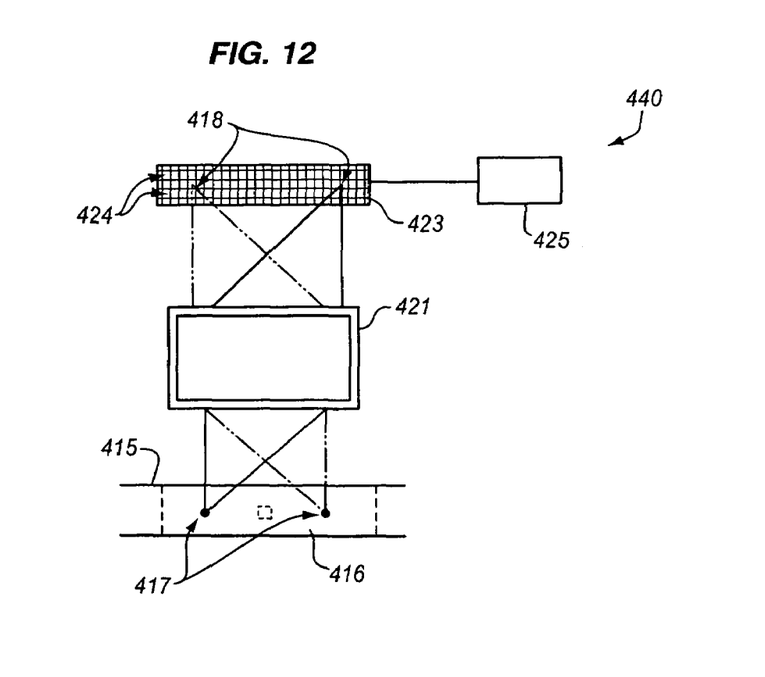
FIG. 12 illustrates how particles are imaged on a two-dimensional CMOS array according to the invention by the particle counter of either FIG. 5 or 11.

FIG. 12 illustrates how particles are imaged on a two-dimensional CMOS or CCD array according to the invention. Laser beam 415 is directed through sensing region 416, indicated by the dotted lines. The light scattered by particles, such as 417, is imaged by imaging system 421 and detected by detector 440. Detector 440 includes pixel array 423 and associated electronics 425. Particles 417 in sensing region 416 are imaged at 418 on array 423 and a particle image scans completely across a particular element, such as 424, during transit of the particle through the laser beam 415. The energy of a particle at a particular time is localized as much as possible to a single array pixel 424 by imaging system 421. In the preferred embodiment described herein, the particles are ≦0.1 µm, whereas each pixel of the Micron CMOS array 423 discussed below views an area of 12×12 µm in the fluid. The Knollenberg (1992) article referenced above gives the formula for the effective image size corresponding to the scattered light from the particle focused onto the detector. This scattered light spot size equals the laser beam depth (depth of field) times the numerical aperture of the collection optics; the preferred design utilizes a 24 µm laser beam waist with a collection optics NA of 0.5, to match the Micron CMOS 12 µm pixel size. Imaging system 421 may be imaging system 150 of FIG. 1, 270 of FIG. 6, 350 of FIG. 11, or any other suitable imaging system. Those skilled in the art will know how to design such imaging systems based on the disclosure herein.

Figure 13:
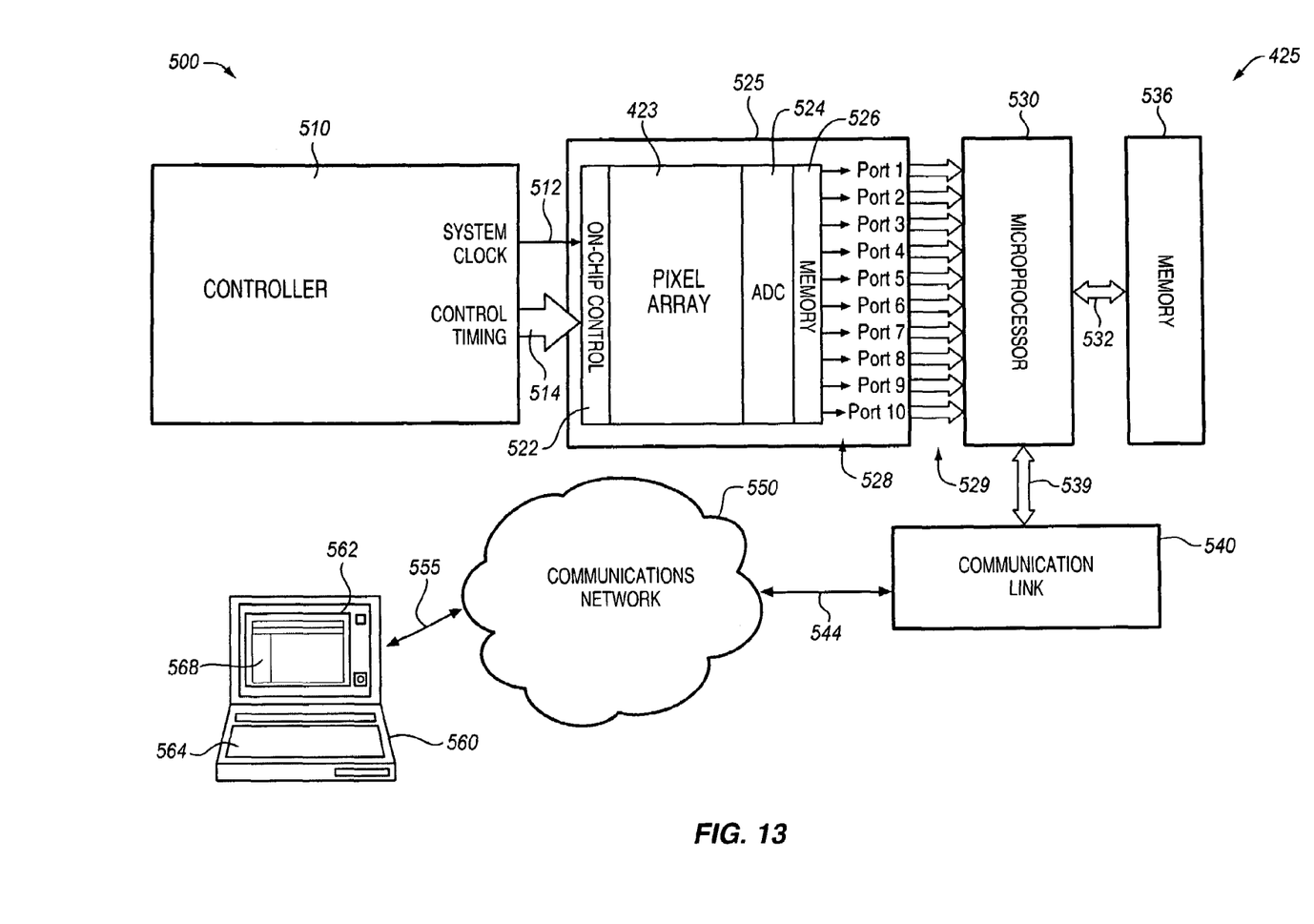
FIG. 13 shows a block circuit diagram of the preferred embodiment of the sensor and associated electronics according to the invention.

FIG. 13 illustrates the preferred sensor electronics embodiment 500, which include pixel array 423 and associated electronics 425. Senor electronics 500 comprises sensor controller 510, CMOS sensor 525, microprocessor 530, memory 536, communications link 540, communications network 550, and computer 560. In the preferred embodiment, sensor 525 is an MT9M413C36STM 1.3 megapixel CMOS active-pixel digital image sensor available from Micron Technologies, Inc., 8000 South Federal Way, P.O. Box 6, Boise, Id. 83707-006. A description of this detector may be downloaded at http://www.micron.com/products/imaging/products/MT9M413.html, which description, Micron Document No. MT9M43C365TC.fm—ver. 3.0 January 2004 EN, is hereby incorporated by reference to the same extent as though fully disclosed herein. This sensor is preferred because it is extremely fast, capable of 500 frames per second, and permits simultaneous exposure of the entire pixel array. As discussed more fully in the above Micron reference, sensor chip 525 includes on-chip control electronics 522, pixel array 423, 1280 analog-to-digital converters 524, on-chip memory 526, and ten ten-bit-wide output ports 528. As indicated more fully in the Micron reference, controller 510 is preferably an FPGA, CPLD, ASIC, or other programmable device that provides the system clock signal on line 512 and other timing signals on lines 514 to chip 525. The timing is described in the Micron reference. Microprocessor 530 is preferably a high-speed microprocessor, such as a Pentium™ M available from Intel Corporation, and memory 536 is preferably a combination of RAM and non-volatile memory. Microprocessor 530 receives the output from ports 528 via lines 529 and communicates with memory 536 via lines 532. Following software instructions stored in memory 536, microprocessor 530 processes the data from chip 525 to an output signal representative of the particles 417 to communications network 550 via communications link 540. Preferably, communications link 540 is an Ethernet serial port, and communications network 550 is a local area network (LAN), the Internet, or any other suitable network. Computer 560 preferably includes one or more input devices 564 and a display 562. Computer 560 may be a PC, a workstation, or any other suitable computer. Computer 560 communicates with network 550 via communication lines 555, which in turn communicates with communication link 540 via communication lines 544. Communication lines 555 and 544 may be data lines, telephone cable, wireless, or any other conventional communication system. In the preferred embodiment, the data processing software stored in memory 536 comprises algorithms designed to derive particle size and concentration from the data received on lines 529. Preferably, the image data is used to define a plurality of particle size channels and the number of particles counted in each such channel, which are displayed as data 568 on display 562.

A key aspect of the invention is that it provides high intensity light over a large sensing cross-section, where the sensing cross-section is a cross-sectional area through the center of laser beams in FIG. 4 in a plane perpendicular to the optic axis of the collection optics. In the preferred embodiment, there are 27 laser beams, each having a waist of 24 microns, with the laser having a power of about 70 milliwatts, at 660 mm wavelength, and the beams spread across an area of 1.5 mm to 3 mm in the vertical direction in FIG. 4 and 2 mm to 4 mm in the horizontal direction. Thus, the sensing cross-section is approximately 27×24 microns or about 0.648 mm by 4 mm, or about 2.6 square mm, not accounting for beam divergence away from the waist. The laser power divided by the beam's circular cross-section yields 155 W/$mm^2$ at the beam waist. In the state-of-the-art prior art OPCs, the maximum sensing area with a corresponding light intensity was about 0.05 square mm. According to the invention, the sensing area is 0.5 square mm or more, and more preferably 1 square mm or more, and most preferably 2 square mm or more. The light intensity over this area is preferably at least 10 W/$mm^2$ or more, more preferably 20 W/$mm^2$ or more, and most preferably 30 W/$mm^2$ or more. Thus, the invention increases the sensing area by at least a factor of ten. The large sensing area permits a large volume of fluid to be examined, greatly decreasing the time it takes to detect particles of a given size, or greatly decreasing the smallest size of a particle that can be detected, or both. The system according to the invention increases the signal-to-noise ratio by a factor of one hundred or more as compared with present state-of-the-art OPCs, and allows the lower limit of sizing to be extended accordingly.

It is a feature of the invention that stray light from the flow cell walls, including that from multiple reflections, is significantly reduced. Note in the photograph of the multiple laser beam pattern in water illustrated in FIG. 4, essentially only molecular scatter from the beam was visible; as suggested by the illustration, the image is very black between the beams. This is due to the unique feature that the back wall of the flow cell, as viewed by the detector, can be placed an arbitrary distance upstream of the sample volume; thus, stray light from the back is negligible. In fact, in the embodiment of the flow cell of FIGS. 7-10, there is no solid back wall, because the detector is looking down the hollow inlet tube 251. Referring to FIG. 6 and FIGS. 7-10, the fluid flows through said sample chamber in a first direction 262 (FIG. 6) and the detector 282 detects light scattered from said particles in the same first direction. The optical collection system 270 has an optical axis 277. The ability to move the flow cell wall an arbitrary distance upstream of the sample volume 250 means that, in a direction along optical axis 277 opposite to the direction of the detector 282 from the sample chamber 240, there is no flow cell wall from which stray light sufficient to create optical noise can enter the detector.

Now that a method and apparatus capable of effectively utilizing a detector array having thirty or more detector elements has been disclosed, those skilled in the art may design many other OPCs that utilize the invention. For example, now that it is known that the single thin-waisted laser beam geometry in the conventional high-end OPC was part of the problem of detecting smaller particles rather than a solution to the problem, one skilled in the art will recognize that designs using a larger particle sensing area may be employed to advantage in combination with larger arrays. For example, the particle counter design as disclosed in U.S. Pat. No. 4,728, 190, referenced above, can be used with a larger array, such as a CCD or CMOS array, since it has a relatively large sensing area as compared to other liquid particle counters. Similarly, instead of reflecting a single laser beam as disclosed herein to provide a multiple beam pattern in the sensing area, a plurality of lasers may be used. In particular, with the invention, a plurality of relatively inexpensive, low power laser diodes may be used instead of a single expensive, high power laser. Further, now that the particular advantages that a CMOS array has in an OPC are known, those skilled in the art may utilize a CMOS array in many other particle counter designs.

There has been described a novel particle counter system that utilizes a detection array having thirty or more elements, such as a CCD array or a CMOS array. It should be understood that the particular embodiments shown in the drawings and described within this specification are for purposes of example and should not be construed to limit the invention, which will be described in the claims below. Further, it is evident that those skilled in the art may now make numerous uses and modifications of the specific embodiments described, without departing from the inventive concepts. It is also evident that the methods recited may in many instances be performed in a different order, or equivalent structures and processes may be substituted for the various structures and processes described. Consequently, the invention is to be construed as embracing each and every novel feature and novel combination of features present in and/or possessed by the invention herein described.

What is claimed as new and desired to be protected by Letters Patent of the United States is:

1. An optical particle counter for optically detecting single unconstrained particles of less than one micron in size suspended in a flowing fluid, said optical particle counter comprising:
    a sample chamber having a fluid inlet and a fluid outlet;
    a source of light;
    a light-directing optical system directing said light through said sample chamber;
    an optical collection system located to collect light scattered by said particles in said fluid flowing through said sample chamber; and
    a detection system located to detect light collected by said optical collection system, said detection system including an optical detector producing an electric signal characteristic of the number of said single particles of less than one micron in size which are detected;
    wherein said optical detector comprises a CMOS imager; wherein said optical collection system collects said light about an optical axis, and wherein said fluid flows through said sample chamber in the direction of said optical axis.

2. A device as in claim 1 wherein said fluid is a liquid.

3. A device as in claim 1 wherein said source of light comprises a laser beam.

4. A device as in claim 1 wherein in a direction along said optical axis opposite to the direction of said detector from said sample chamber, said sample chamber has no sample chamber wall from which stray light sufficient to create optical noise can enter said detector.

5. A device as in claim 1 wherein said detection system comprises a microprocessor.

6. A device as in claim 1 wherein said detection system comprises a computer.

7. A device as in claim 3 wherein said light-directing optical system comprises redirection optics for directing and refocusing said laser beam through said sample chamber a plurality of times.

8. A device as in claim 7 wherein said redirection optics comprise a plurality of mirrors.

9. A device as in claim 8 wherein said plurality of mirrors are located to direct said laser beam through said sample chamber 10 or more times.

10. A device as in claim 9 wherein said plurality of mirrors are located to direct said laser beam through said sample chamber 25 or more times.

11. A device as in claim 6 wherein said source of light comprises a plurality of lasers producing a plurality of laser beams, and said light-directing optical system comprises an optical system for directing said plurality of laser beams through said sample chamber.

12. A device as in claim 7 wherein said laser beam passes through said sample chamber in a plane perpendicular to said optical axis.

13. A device as in claim 1 wherein said fluid flow is in a direction substantially parallel to said optical axis.

14. A device as in claim 2 wherein said liquid is water, and said sample chamber comprises a fused silica glass window or lens.

15. A method of detecting single unconstrained particles of less than one micron in size in a fluid flow, said method comprising:
    flowing said fluid containing said single unconstrained particles of less than one micron in size;
    directing a laser beam through said fluid flow;
    collecting light scattered by said particles in said fluid, wherein said collecting comprises collecting said light about an optical axis, and said flowing comprises flowing said fluid in the direction of said optical axis; and
    detecting said collected light with a CMOS imager and outputting a signal from said CMOS imager that is characteristic of a parameter of said single particles.

16. A method as in claim 15 wherein said directing comprises passing said laser beam through said fluid flow and refocusing the beam a plurality of times.

17. A method as in claim 16 wherein said passing comprises passing said laser beam through said fluid flow three or more times in the same plane.

18. A method as in claim 17 wherein said collecting comprises collecting said scattered light about said optical axis perpendicular to said plane.

19. A device for optically detecting single unconstrained particles of less than one micron in size suspended in a flowing fluid, said device comprising:
    a sample chamber having a fluid inlet and a fluid outlet;
    a multiple beam laser optical system for providing a plurality of laser beams in said sample chamber;
    an optical collection system located to collect light scattered by said single particles of less than one micron in size in fluid flowing through said sample chamber; and
    a detection system located to detect light collected by said optical collection system, said detection system including an optical detector producing an electric signal characteristic of the number of said single particles detected;
    wherein said optical detector has thirty or more optical detector elements; and wherein said fluid flows through said sample chamber in a first direction and said detector detects light scattered from said particles in said first direction.

20. A device as in claim 19 wherein said multiple beam laser optical system comprises a laser producing said laser beam and an optical redirection device for directing and refocusing said laser beam back through said sample chamber after it has passed through said chamber once.

21. A device as in claim 20 wherein said optical redirection device comprises a mirror.

22. A device as in claim 21 wherein said optical redirection device comprises a plurality of mirrors.

23. A device as in claim 19 wherein said optical collection system has an optical axis, and said laser beams lie in a plane perpendicular to said optical axis.

24. A device as in claim 19 wherein said laser beams in said sample chamber, said optical collection system, and said detector define a sensing region, said sensing region having a cross-sectional area in a plane parallel to said laser beams, which area is 0.5 square millimeters or more.

25. A device as in claim 24 wherein said area is 1 square millimeter or more.

26. A device as in claim 24 wherein said area is 2 square millimeters or more.

27. A device as in claim 24 wherein said multiple beam laser optical system comprises a plurality of lasers providing said laser beams.

28. A device as in claim 19 wherein said optical detector comprises a CCD pixel array.

29. A device as in claim 19 wherein said optical detector comprises a CMOS pixel array.

30. A device as in claim 19 wherein said optical detector comprises a two-dimensional pixel array.

31. A device as in claim 19 wherein there are ten or more of said laser beams.

32. A device as in claim 19 wherein said optical collection system has an optical axis, and, in a direction along said optical axis opposite to the direction of said detector from said sample chamber, said sample chamber has no sample chamber wall from which stray light sufficient to create optical noise can enter said detector.

33. A device for optically detecting single unconstrained particles suspended in a flowing fluid, said device comprising:
   a sample chamber having a fluid inlet and a fluid outlet;
   a light source for providing one or more light beams in said sample chamber;
   an optical collection system located to collect light scattered by said particles in said light beams in said sample chamber;
   a detection system located to detect light collected by said optical collection system, said detection system including an optical detector producing an electric signal characteristic of the number of said single particles detected; said optical detector has thirty or more optical detector elements; and
   said one or more light beams, said optical collection system, and said optical detector defining a particle sensing area within said sample chamber in which the intensity of light is at least 10 watts per square millimeter, said sensing area having an area of 0.5 square mm or more.

34. A device as in claim 33 wherein said sensing area is one square mm or more.

35. A device as in claim 34 wherein said light source includes a plurality of mirrors.

36. A device as in claim 33 wherein said sensing area is two square mm or more.

37. A device as in claim 33 wherein said light source comprises a laser.

38. A device as in claim 33 wherein said light source comprises a plurality of lasers.

39. A device as in claim 33 wherein said optical detector comprises a CCD pixel array.

40. A device as in claim 33 wherein said optical detector comprises a CMOS pixel array.

41. A device as in claim 33 wherein said optical detector comprises a two-dimensional pixel array.

42. A device as in claim 33 wherein said fluid flows through said sample chamber in a first direction and said detector detects light scattered from said particles in said first direction.

43. A device as in claim 33 wherein said optical collection system has an optical axis, and, in a direction along said optical axis opposite to the direction of said detector from said sample chamber, said sample chamber has no sample chamber wall from which stray light sufficient to create optical noise can enter said detector.

44. A device for optically detecting single unconstrained particles of less than one micron in size suspended in a flowing fluid, said device comprising:
   a sample chamber having a fluid inlet and a fluid outlet;
   a light source for providing one or more light beams in said sample chamber;
   an optical collection system located to collect light scattered by said single particles of less than one micron in size in fluid flowing through said sample chamber; and
   a detection system located to detect light collected by said optical collection system, said detection system including an optical detector producing an electric signal characteristic of the number of said single particles detected;
   wherein said optical detector has thirty or more optical detector elements; and wherein said collection system collects said light about an optical axis, and wherein said fluid flows through said sample chamber in the direction of said optical axis.

45. A device as in claim 44 wherein said optical detector comprises a CCD pixel array.

46. A device as in claim 44 wherein said optical detector comprises a CMOS pixel array.

47. A device as in claim 44 wherein said optical detector comprises a two-dimensional pixel array.

48. The device of claim 44 wherein said light source is a laser for providing a laser beam in said sample chamber.

* * * * *